United States Patent [19]

Robach et al.

[11] 4,388,321

[45] Jun. 14, 1983

[54] METHOD FOR INHIBITING GROWTH OF FOOD POISONING ORGANISMS

[75] Inventors: Michael C. Robach, St. Peters, Mo.; Quentin E. Thompson, Belleville, Ill.

[73] Assignee: Monsanto Company, St. Louis, Mo.

[21] Appl. No.: 290,446

[22] Filed: Aug. 6, 1981

[51] Int. Cl.³ .................. A01N 43/02; A23L 3/34
[52] U.S. Cl. .................................. 424/279; 426/532
[58] Field of Search ........................ 424/285, 279; 260/343.6; 426/532

[56] References Cited

U.S. PATENT DOCUMENTS 3,331,837 7/1967 Lehmann .................. 260/343.6
4,175,089 11/1979 Heiba et al. ................ 260/343.6

OTHER PUBLICATIONS

Kuenzel et al., Chemical Abstracts vol. 69 (1968): 74718m.
Sakurai et al., Chemical Abstracts vol. 69 (1968): 94792j.
Dal Pozzo et al., Chemical Abstracts vol. 91 (1979): 84063n.

*Primary Examiner*—Douglas W. Robinson
*Attorney, Agent, or Firm*—R. E. Wexler; G. R. Beck

[57] ABSTRACT

Certain furanones are shown to inhibit growth of food poisoning organisms in laboratory culture media.

6 Claims, No Drawings

METHOD FOR INHIBITING GROWTH OF FOOD POISONING ORGANISMS

BACKGROUND OF THE INVENTION

This invention relates to novel compounds capable of inhibiting growth of food spoilage and food poisoning organisms which decrease the storage life of food products which normally spoil or lose flavor. In particular, this invention is related to a method of inhibiting the growth of food spoilage organisms.

Deterioration due to spoilage organisms occurs extensively in untreated foodstuffs such as bakery products, fish, meats, fruits, vegetables and dairy products. Industrial food processing plants incur losses both in the form of returned, deteriorated products and of impaired sales owing to inferior keeping quality of the products. Consumers, also, are caused direct losses by such deterioration but, in addition, they also run health risks because of the toxins formed by pathogens which may already be produced before the growth of such pathogens is observable. Heretofore, attempts have been made to prevent or inhibit the growth of food spoilage and food poisoning organisms by using packaging materials which have been treated by a variety of substances and by intensifying plant hygiene and thus reducing the amount of pathogen and food spoilage organism infection. Intensified food plant hygiene has successfully lowered the frequency of food spoilage organisms to a significant degree. It is impossible, however, in practice, to solve the problem completely by this approach, since it has not been possible to reduce to a sufficiently low level the organism infection by which food is contaminated even by such expedients as filtration of intake air and ultraviolet light treatment.

Aerobic microorganisms are deposited on the surface of foods through post-processing contamination from the air, from the hands of an operator, from equipment and utensils and other means. Typical examples are the formation of slime on the surfaces of slaughtered animal carcasses and the growth of bacterial colonies on sliced sausages.

Since post-processing microbial contamination, in most cases, remains on the surface of the food or feed, aerobic microorganisms generally can multiply only on the superficial layers of the food or feed. Accordingly, the measures aimed at fighting such microorganisms are concentrated on the superficial layer and the desired preventative effect can thereby be achieved. The procedures applied heretofore for the purpose of applying chemical or equivalent inhibitors of microorganisms growth on the superficial layer of food products have been by dipping the food in a solution of chemical preservative, spraying a chemical preservative solution onto the surface of food or feed and impregnating packaging material with a chemical preservative. A wide variety of such chemical preservatives have heretofore been used.

For instance, U.S. Pat. No. 2,711,976 suggests the use of amino acids to increase the resistance of custard foods to spoilage organisms and Staphylococcus aureus. U.S. Pat. No. 2,898,372 suggests calcium acetate propionate as a bread treating composition. U.S. Pat. No. 2,866,819 suggests the use of sorbic acid as a preservative in foods. U.S. Pat. No. 2,910,368 discloses the use of EDTA with sorbic acid to increase the shelf life of vegetables. U.S. Pat. No. 2,992,114 suggests the use of sorbic acid and a mild heat treatment for the preservation of fruits and vegetables. In a paper published in Applied Microbiology, Volume 18, pages 68–75 (July, 1969), Preonas et al reported on the use of a mixture of sorbic acid and propionic acid to retard the growth of Staphylococcus aureus on the surfaces of custard pies.

In accordance with the present invention, there is described and claimed a method of inhibiting the growth of pathogen and spoilage organisms which decrease the shelf life of foods by treating same with furanones. Furanones are frequently described in the literature as butyrolactones.

SUMMARY OF THE INVENTION

The present invention describes the use of furanones to inhibit the growth of food poisoning and spoilage organisms which render food products unpalatable or unsafe to eat.

The means for accomplishing the purpose of this invention comprises treating food products with a furanone. Especially preferred furanones are those which are substituted by an ethyl or ethenyl group in the fifth ring position. Members of this group of compounds which would be expected to inhibit the growth of microorganisms are represented by the formula:

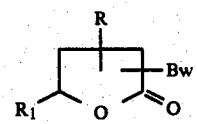

wherein R represents hydrogen or a substituted or unsubstituted alkyl substituent of up to 10 carbon atoms; B represents a double bond; $R_1$ represents an ethenyl substituent; and w represents 0 or 1. Thus, R may represent hydrogen, methyl, ethyl, propyl, butyl, amyl, hexyl, heptyl, octyl, nonyl and decyl substituents. Such substituents may be either straight- or branched-chain and may, themselves, contain substituents which are not inconsistent with the antimicrobial action of the compounds in a food environment.

Especially preferred furanones are those represented by the formula

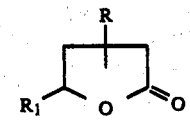

wherein R represents hydrogen and $R_1$ represents ethenyl, i.e. 5-ethenyl-2(5H)-furanone.

Other especially preferred furanones are those represented by the formulas

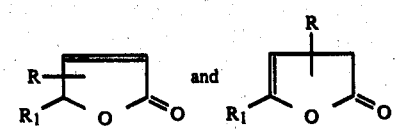

wherein R represents hydrogen and $R_1$ represents ethyl, i.e. 5-ethyl-2(5H)-furanone and 5-ethyl 2(3H) furanone.

The preparation of furanones has been previously published in the literature. For example, U.S. Pat. No. 3,992,417, U.S. Pat. No. 4,158,741 and U.S. Pat. No. 4,175,089 disclose the preparation of γ-butyrolactones by reaction of olefins and a compound containing a carboxylate moiety, e.g. acetic acid. 5-Ethenyl-2(5H)-furanone (i.e. γ-vinyl-γ-butyrolactone) is prepared by the reaction of butadiene and acetic acid. The furanones are used for a variety of industrial uses, e.g., preparation of saturated and unsaturated fatty acids, flavoring agents and antioxidants.

It is contemplated that the application of the described furanones to a food product would be by dipping or otherwise immersing the food product in the furanone or by spraying the furanone onto the food product.

Among the microorganisms against which the furanones are contemplated as being effective as growth inhibitors are the nonlactic acid gram positive bacteria such as *Staphylococcus aureus, Bacillus cereus, Clostridium perfringens* and other clostridial species and the Micrococcus species. Additionally, the described furanones are contemplated to be effective growth inhibitors of gram negative bacteria such as Salmonella species, *Escherichia coli, Vibrio parahemolyticus* and species of Pseudomonas, Alcaligines and Flavobacterium. Furthermore, the furanones are contemplated to be a growth inhibitor, although to a lesser extent than with microorganisms, against yeasts such as *Candida albicans, Saccharomyces cerevisiae* and against molds such as Aspergillus, *Penicillium italicum* and *Fusarium roseum*. Among the food products which would be particularly benefited by treatment with furanones are foods which have high water activity and which are subject to temperature abuse, i.e. improper storage and transportation temperature conditions. Examples of such foods are packaged meat products, dairy products, prepared salad products and prepared entree products of all types.

Among feed products which may be benefited by treatment with furanones are those byproduct feeds which are subject to pathogen attack, e.g. fishmeal, poultry byproduct meal and rendered animal wastes.

The concentration of furanone compound which is contemplated as being effective in the treatment of food or feed products is generally in the range of from about 0.005% to about 1.5%, more particularly from about 0.05% to about 0.3% and, especially, from about 0.1% to about 0.2% based on the weight of the substrate. The specific concentration of furanone with which a particular microorganism is treated will vary, depending upon the specific microorganism, its environment, the substrate involved and the presence of other preservative agents.

EXAMPLES OF PREFERRED EMBODIMENTS

In the Table, 5-ethenyl-2(5H)-furanone was tested for anti-microbial activity against *Salmonella infantis,* a common gram negative food poisoning bacteria. The testing was conducted at pH5 in trypticase soy broth at 37° C. The growth of the bacteria was monitored using standard spectrophotometric methods daily for six days. The results are reported in the Table as optical density (i.e. absorbence at 550 nanometers). The values are approximate, having been transposed from graphic form. The results indicate that 5-ethenyl-2(5H)-furanone is an effective inhibitor of *S. infantis.*

TABLE

| Additive | Salmonella infantis 10,000 cells/ml Absorbance at 550 Nanometers | | | | | | |
|---|---|---|---|---|---|---|---|
| | 0 Days | 1 Day | 2 Days | 3 Days | 4 Days | 5 Days | 6 Days |
| Control | 0.1 | 0.8 | 0.9 | 0.8 | 0.8 | 0.8 | 0.8 |
| 0.1% 5-ethenyl-2(5H)—furanone | 0.0 | 0.1 | 0.6 | 0.6 | 0.7 | 0.7 | 0.6 |
| 0.2% 5-ethenyl-2(5H)—furanone | 0.0 | 0.0 | 0.1 | 0.3 | 0.4 | 0.5 | 0.6 |

We claim:

1. Method of inhibiting growth of yeasts in a food or feed product which comprises contacting said yeast with an effective growth inhibiting amount of a furanone represented by the formula

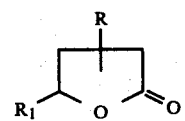

wherein:
R represents hydrogen or alkyl having up to 10 carbon atoms; and
$R_1$ represents an ethenyl group.

2. Method of inhibiting growth of yeasts in a food or feed product which comprises contacting said yeast with an effective growth inhibiting amount of a furanone represented by the formula

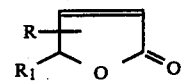

wherein:
R represents hydrogen or alkyl having up to 10 carbon atoms; and
$R_1$ represents an ethyl group.

3. Method of inhibiting growth of yeasts in a food or feed product which comprises contacting said yeast with an effective growth inhibiting amount of a furanone represented by the formula

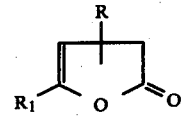

wherein:
R represents hydrogen or alkyl having up to 10 carbon atoms; and
$R_1$ represents an ethyl group.

4. Method of claim 1 wherein R is hydrogen.
5. Method of claim 2 wherein R is hydrogen.
6. Method of claim 3 wherein R is hydrogen.

* * * * *